(12) United States Patent
Osborne (10) Patent No.: US 6,355,657 B1
(45) Date of Patent: Mar. 12, 2002

(54) SYSTEM FOR PERCUTANEOUS DELIVERY OF OPIOID ANALGESICS

(75) Inventor: David W. Osborne, Fort Collins, CO (US)

(73) Assignee: Atrix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 09/475,094

(22) Filed: Dec. 30, 1999

Related U.S. Application Data

(60) Provisional application No. 60/114,224, filed on Dec. 30, 1998.

(51) Int. Cl.[7] .............................................. A61K 31/47
(52) U.S. Cl. ...................................................... 514/327
(58) Field of Search .......................................... 514/327

(56) References Cited

U.S. PATENT DOCUMENTS

| | | | |
|---|---|---|---|
| 5,116,847 A | | 5/1992 | Gilbert et al. ............... 514/327 |
| 5,667,773 A | * | 9/1997 | Farrar et al. .............. 424/78.05 |
| 5,994,372 A | | 11/1999 | Yaksh ........................ 514/327 |

OTHER PUBLICATIONS

Franz, T.J. (Mar. 1975). "Percutaneous Absorption. On the Relevance of In Vitro Data," *J. Invest. Dermatol.* 64(3):190–195.

Osborne, D.W. and Amann, A.H. (1990). "Topical drug delivery formulations," Marcel Dekker, Inc.: New York, Table of Contents, pp. v–x.

Osborne, D.W. and Ward, A.J.I. (Jul. 1995). "Lyotropic Liquid Crystals as Topical Drug Delivery Vehicles," *Intl. J. Pharm. Advances* 1(1):38–45.

Osborne, D.W. and Henke, J.J. (Nov. 1997). "Skin Penetration Enhancers Cited in the Technical Literature," *Pharm. Technol.* 58–66.

Roberts, M.S. and Walters, K.A. (1998). "Dermal absorption and toxicity assessment," Marcel Dekker, Inc.: New York, Table of Contenets, pp. v–vii.

* cited by examiner

*Primary Examiner*—Dwayne C. Jones
(74) *Attorney, Agent, or Firm*—Morrison & Foerster LLP (57) ABSTRACT

Compositions and methods for the topical delivery of loperamide hydrochloride are disclosed. Novel solvent mixtures have been found to be beneficial in enhancing the penetration of loperamide hydrochloride through the skin.

43 Claims, 8 Drawing Sheets

SYSTEM FOR PERCUTANEOUS DELIVERY OF OPIOID ANALGESICS

CROSS-REFERENCES TO RELATED APPLICATIONS

This application claims benefit of Prov. No. 60/114,224 filed Dec. 30, 1998.

FIELD OF THE INVENTION

The invention relates to methods and compositions for the percutaneous delivery of opioid analgesics through the epidermis and, more specifically, to methods and compositions for the percutaneous delivery of loperamide hydrochloride through the epidermis.

BACKGROUND OF THE INVENTION

Opioid analgesics such as morphine are known for the ability to relieve pain. This pharmacological effect occurs in at least three ways: (1) reduction of the central perception of pain probably at the thalamic level, (2) alteration of the reaction to pain probably at the level of the cerebral cortex, and (3) elevation of the pain threshold by inducing sedation or sleep.

Certain opioids are also known to be antihyperalgesic. As an antihyperalgesic opioid, loperamide hydrochloride is effective in treating pain and hypersensitivity to painful stimuli associated with inflammatory skin conditions. Due to its high affinity for peripheral opioid receptors and poor ability to penetrate the central nervous system, loperamide hydrochloride is an excellent candidate for topical administration of an antihyperalgesic.

The Merck index (Twelfth Edition, Merck & Co., Inc., Whitehouse Station, N.J., 1996) presents the solubility of loperamide hydrochloride in a variety of solvents, stated as grams per 100 mL solvent. The stated values are: water (at physiological pH) 0.002; water (pH 1.7) 0.14; citrate-phosphate buffer (pH 6.1) 0.008; citrate-phosphate buffer (pH 7.9) less than 0.001; methanol 28.6; ethanol 5.37; 2-propanol 1.11; dichloromethane 35.1; acetone 0.20; ethyl acetate 0.035; diethyl ether less than 0.001; hexane less than 0.001; toluene 0.001; N,N-dimethylformamide 10.3; tetrahydrofuran 0.32; 4-methyl-2-pentanone 0.020; propylene glycol 5.64; polyethylene glycol 400 1.40; dimethylsulfoxide 20.5; 2-butanone 0.18.

U.S. Pat. No. 5,116,847 (issued May 26, 1992) describes compositions and methods for the treatment of respiratory disease symptoms. An array of chemical structures are disclosed, including loperamide, loperamide salts, and loperamide N-oxides. Compositions for nasal administration include aqueous benzalkonium chloride, thimerosal, or phenylmercuric acetate.

U.S. Pat. No. 5,667,773 (issued Sep. 16, 1997) describes topical anti-hyperalgesic compositions comprising one of an array of chemical compounds. The compositions further comprise a film-forming polymer material and an aqueous pharmaceutically acceptable carrier. The chemical compounds include loperamide.

Osborne and Henke (*Pharm. Technol.* 58–66, November 1997) discusses skin penetration enhancers cited in the technical literature for the transdermal delivery of pharmaceuticals.

Roberts and Walters ("Dermal Absorption and Toxicity Assessment", Marcel Dekker, Inc., New York, 1998) and Osborne and Amann ("Topical Drug Delivery Formulations", Marcel Dekker, Inc., New York, 1990) are general texts teaching the topical administration of pharmaceuticals and cosmetics.

There exists a need for improved compositions and topical administration methods for opioid analgesics generally, and for loperamide hydrochloride in particular.

SUMMARY OF THE INVENTION

An effective dermal algesic or antihyperalgesic composition would comprise an opioid and a vehicle for delivering the opioid into the skin. There are numerous obstacles to achieving such a composition.

The primary obstacle for topical administration of pharmaceuticals is to deliver a topically-applied substance through the stratum corneum layer of the epidermis. The stratum corneum is a highly resistant layer comprised of protein, cholesterol, sphingolipids, free fatty acids and various other lipids as well as living cells. Applicants have discovered a second obstacle which must be overcome, the delivery of a sufficient quantity of the substance through the stratum corneum to achieve a minimum effective concentration in the skin where peripheral opioid receptors, i.e. nerve tissue at the dermal/epidermal junction, are located. Applicants have further discovered that a third obstacle is maintaining a sufficient concentration of the active substance in the skin where peripheral opioid receptors are located for a minimum effective period of time to achieve the desired response. That is, it is not sufficient that a minimum concentration merely be reached; it must be sustained for a minimum time period.

It is Applicants' unique discovery to have identified the limiting factors of concentration and duration of exposure and to have discovered formulations which penetrate into and through the stratum corneum and deliver the active substance to the skin where nerve tissue is located in sufficient quantity and duration.

The invention relates generally to loperamide hydrochloride compositions and methods for the use of loperamide hydrochloride compositions. Preferably, the compositions contain dissolved loperamide hydrochloride at a concentration of at least about 1% (w/w) of the composition. More preferably, the concentration of dissolved loperamide hydrochloride is greater than about 16% (w/w), even more preferably is at least about 20% (w/w), and most preferably is at least about 30% (w/w). Compositions preferably display an in vitro rate of penetration of loperamide hydrochloride through the stratum corneum is at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. Percent compositions of the various components in the inventive compositions are preferably determined at 22° C.

A preferred embodiment is directed towards a composition comprising dissolved loperamide hydrochloride, propylene carbonate, and ethanol, wherein the concentration of dissolved loperamide hydrochloride is at least about 1% (w/w) of the composition. The composition preferably has an in vitro rate of penetration of loperamide hydrochloride through the stratum corneum is at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

An alternative embodiment is directed towards a composition comprising dissolved loperamide hydrochloride, propylene glycol, and ethyl acetate, wherein the concentration of dissolved loperamide hydrochloride is at least about 1% (w/w) of the composition. The composition preferably has an in vitro rate of penetration of loperamide hydrochloride through the stratum corneum is at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

An alternative embodiment is directed towards a composition comprising dissolved loperamide hydrochloride, N-methyl-2-pyrrolidone, and ethanol, wherein the concentration of dissolved loperamide hydrochloride is at least about 1% (w/w) of the composition. The composition preferably has an in vitro rate of penetration of loperamide hydrochloride through the stratum corneum is at least about 0.3 $\mu$g per cm$^2$ is 5 per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise water, or water and propylene glycol. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

Preferred compositions contain propylene carbonate and ethanol or a blend of N-methyl-2-pyrrolidone, ethanol, and propylene glycol or water or the blend of N-methyl-2-pyrrolidone, ethanol, propylene glycol and water. For example, one composition may comprise between about 25% and about 70% ethanol or propylene carbonate, between about 25% and about 70% water, between about 1% and about 10% penetration enhancer and between about 1% and about 10% opioid analgesic, wherein the percentages total to 100%. Another composition may comprise between about 10% and about 70% ethanol, between about 10% and about 70% propylene carbonate, between about 1% and about 10% penetration enhancer, and between about 1 % and about 10% opioid analgesic wherein the percentages total to 100%. Two particularly preferred compositions are: (1) 10% N-methyl-2-pyrrolidone, 10% propylene glycol, 40% ethanol, 30% water, 5% loperamide hydrochloride, 5% enhancing, gelling, and preserving agents; and (2) 45% propylene carbonate, 45% ethanol, 5% loperamide hydrochloride, 5% gelling enhancing and preserving agents.

The invention is also directed towards methods for inducing analgesia or antihyperalgesia in mammals, humans, or non-human mammals, and preferably in humans. Alternatively, the invention is directed towards methods for inducing analgesia or antihyperalgesia in non-mammalian animals such as birds and amphibians. Commercially important birds such as chickens and turkeys may be potential subjects for the inventive compositions and methods.

An embodiment is directed towards a method of inducing analgesia or antihyperalgesia in humans or in human epidermis, comprising topically applying a composition to the skin in a dosage effective to cause analgesia or antihyperalgesia, wherein: the composition comprises dissolved loperamide hydrochloride, propylene carbonate, and ethanol; the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

An alternative embodiment is directed towards a method of inducing analgesia or antihyperalgesia in humans or in human epidermis, comprising topically applying a composition to the skin in a dosage effective to cause analgesia or antihyperalgesia, wherein: the composition comprises dissolved loperamide hydrochloride, propylene glycol, and ethyl acetate; the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

An alternative embodiment is directed towards a method of inducing analgesia or antihyperalgesia in humans or in human epidermis, comprising topically applying a composition to the skin in a dosage effective to cause analgesia or antihyperalgesia, wherein: the composition comprises dissolved loperamide hydrochloride, N-methyl-2-pyrrolidone, and ethanol; the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour, more preferably is at least about 0.3 $\mu$g per cm$^2$ per hour for one hour after administration, and most preferably is at least about 0.3 $\mu$g per cm$^2$ per hour for six hours after administration. The composition may further comprise a hydrotropic agent. The hydrotropic agent may generally be any hydrotropic agent which functions to increase disorder in the lamellar liquid crystalline structure of the stratum corneum and thus allow increased transdermal transport, and preferably is isopropyl alcohol, propylene glycol, or sodium xylene sulfonate. The composition may further comprise an opioid analgesic. The opioid analgesic may generally be any opioid analgesic, and preferably is morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, or butorphanol. The composition may further comprise moisturizers, humectants, oils, emulsifiers, thickeners, thinners, surface active agents, fragrances, preservatives, antioxidants, vitamins, or minerals. The composition may further comprise water, or water and propylene glycol. The composition may further comprise a penetration enhancer effective to improve the percutaneous penetration of the loperamide hydrochloride into and through the stratum corneum with respect to a composition lacking the penetration enhancer. The penetration enhancer may generally be any penetration enhancer, preferably is oleic acid, oleyl alcohol, ethoxydiglycol, laurocapram, alkanecarboxylic acids, dimethylsulfoxide, polar lipids, or N-methyl-2-pyrrolidone, and more preferably is oleic acid or oleyl alcohol.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DEFINITIONS

The following definitions are provided in order to aid those skilled in the art in understanding the detailed description of the present invention.

"Analgesia" refers to a reduction in the intensity of pain that occurs in response to a normally painful stimulus.

"Antihyperalgesia" refers to a reduction in the intensity of pain that occurs from hyperalgesia.

"Hyperalgesia" refers to a response of increased pain to a stimulus that normally is painful.

"Loperamide hydrochloride" refers to the chemical compound loperamide hydrochloride having the chemical formula $C_{29}H_{34}Cl_2N_2O_2$; 4-(p-chlorophenyl)-4-hydroxy-N,N-dimethyl-α,(α-diphenyl-1-piperidinebutyramide hydrochloride.

"NMP" refers to N-methyl-2-pyrrolidone.

"PC" refers to propylene carbonate.

"Penetration enhancer" refers to any chemical or biochemical which when included in a topically applied loperamide hydrochloride composition enhances amount or rate of percutaneous penetration of loperamide hydrochloride into the nerve tissue of the skin and connected tissue with respect to the loperamide hydrochloride composition lacking the penetration enhancer.

"PG" refers to propylene glycol.

"Subject" refers to an organism to which a loperamide hydrochloride containing composition is applied. Subjects may include humans and non-human mammals, and more preferably refers to humans.

DETAILED DESCRIPTION OF THE INVENTION

The present invention is a composition which can be used in the treatment of pain from cuts, burns, and abrasions, including sunburn.

The objective of the present invention is to provide a composition which can be topically applied to the skin to result in the delivery of an opioid through the stratum corneum to the dermal/epidermal junction for use in the above-listed treatments and as a method for relieving dermal pain and hyperalgesia.

Any composition effective in achieving and maintaining pain relief via topical application to the skin must overcome at least three key hurdles. First, the active substance must pass into and through the stratum corneum. Second, an amount of the active substance passed through the stratum corneum must be sufficient to achieve an effective concentration at the dermal/epidermal junction. Third, the effective concentration of the active substance near the nerves at the dermal/epidermal junction must be maintained for a minimum amount of time.

As noted, the peripheral opioid receptors of nerves in the skin must be exposed to a minimum concentration of loperamide hydrochloride or other opioid for a minimum duration of time before the receptors can be adequately blocked. The concentration of loperamide hydrochloride, for example, must be at least 50 nM, and more preferably, 500 nM or greater, at the opioid receptors before analgesia is obtained. Further, the nerve tissue must be exposed to this level continuously until adequate healing occurs to remove the pain stimulus to prevent breakthrough pain will occur. While re-application of the topical product will occur during the healing process, the concentration of loperamide hydrochloride at the receptors should be maintained at therapeutic levels with topical product re-application occurring not more often than every four hours, and preferably not more often than every six hours. Therefore, any topically applied formulation which is to be effective in vivo must deliver an amount of loperamide hydrochloride which is sufficient to meet these criteria.

Further, a key factor limiting the effectiveness of a formulation in delivering an adequate amount of the active substance to the peripheral opioid receptors is the rate of penetration (flux) through the stratum corneum. Applicant has discovered that for a formulation of loperamide hydrochloride to be effective as an antihyperalgesic, the formulation must be characterized as having an in vitro flux of loperamide hydrochloride of at least 0.3 $\mu g/cm^2/hr$ through intact skin, where the in vitro rate is determined using standard Franz cell technology using excised human skin. Formulations of loperamide hydrochloride, preferably comprising at least one alcohol or organic solvent, which result in a flux rate of at least 0.3 $\mu g/cm^2/hr$ through the stratum corneum and which contain a sufficient amount of dissolved loperamide hydrochloride (preferably 1% (w/w) or greater) will cause analgesia and antihyperalgesia when applied to the skin or inflamed tissue.

Thus, the factors which any preferred formulation would preferably maximize are: (1) solubility of the active substance under ambient conditions; (2) loading of the active substance into and diffusion from the stratum corneum; (3) concentration of the active substance at the peripheral opioid receptors of nerve tissue; and (4) duration of maintenance of the active substance at the nerve tissue (i.e., equilibrium between diffusion into nerve tissue and clearance from the nerve tissue of the active substance is maintained at the target concentration).

Applicants have discovered formulations of particular opioids in aqueous solutions of organic solvents, with or without fatty acid/fatty alcohol penetration enhancers, which can achieve these criteria.

Typically, the formulations will be applied over the skin in a dosage of 0.3 to 1 mL/100 $cm^2$ and rubbed in until no liquid is apparent on the skin. This formulation may be applied at a frequency of every one to two hours, or preferably no more often than 4 to 6 hours, to the areas where analgesia or antihyperalgesic active is desired. Any of the formulations described herein which had penetration qualities in infinite dose experiments described below could be used to deliver an opioid analgesic to the nerve tissue if applied continuously to simulate an infinite dose situation. Further, a formulation which deposits the drug into the stratum corneum and allows the drug to diffuse therefrom at a flux of at least about 0.3 $\mu g/cm^2/hr$ will provide analgesia and antihyperalgesia. A formulation which is made with either a film former such as polyvinyl pyrrolidone or with an enhancer (such as ethoxydiglycol) that allows it to accumulate in the stratum corneum could be applied every 4–6 hours if it delivered a continuous dose of 0.3 $\mu g/cm^2/hr$ from the stratum corneum reservoir to the nerve tissue. As defined herein the term dosage means the amount and frequency of application of the formulation to the skin.

Loperamide hydrochloride Solubility

For clinical applications of topical products one of the factors that limits the penetration rate (flux) of a compound through the stratum corneum is the amount of the active substance which can be "loaded" onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal. This assumes the active does not crystallize on the skin surface prior to penetration. However, up to now, efforts to formulate opioids, such as loperamide hydrochloride, in pharmaceutically acceptable blends of solvents having concentrations of dissolved active substance approaching those found for ethanol have been unsuccessful. Likewise achieving reasonable levels of loperamide hydrochloride solubility when water is present in the formulation have also been unsuccessful. Heretofore, the maximum known solubility of loperamide hydrochloride in saturated water at ambient temperatures has been approximately 0.1% (w/w). Further, solubility of loperamide hydrochloride in most non-aqueous organic solvents being less than 1% (w/w) with the notable exceptions being N-methyl-2-pyrrolidone (16% (w/w)), propylene glycol (9% (w/w)) and ethanol (10% (w/w)). However, as discussed below, Applicants have herein developed formulations of mixtures of water, alcohols and organic solvents, which can contain from up to 30% (w/w) loperamide hydrochloride in solution at ambient temperatures. Applicants have further achieved loperamide hydrochloride solubilities in excess of 5% (w/w) for formulations containing as much as 30% (w/w) water. Greater fluxes through the stratum corneum can be achieved using formulations with these maximized concentrations of loperamide hydrochloride than with solutions of loperamide hydrochloride in water or loperamide hydrochloride in ethanol.

The ability of any solid substance (solute) to dissolve in any liquid substance (solvent) is dependent upon the physical properties of the solute and the solvent. The more similar the physical properties, the greater the solubility of the solute in the solvent. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wal interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

For miscible solvent mixtures such as propylene carbonate and ethanol, or ethanol and water, solute solubility should vary proportionally to the ratio of the solvent blend. For example, if 0.1% of the solute can be dissolved in propylene carbonate, and 10% of the solute can be dissolved in ethanol, then 5% of the solute is expected to dissolve in a 50/50 mixture of propylene carbonate and ethanol. While non-ideal behavior may cause the amount of dissolved solute to be somewhat less than or greater than 5%, it is expected that the value will fall between 0.1 and 10% solute.

Figure 1:
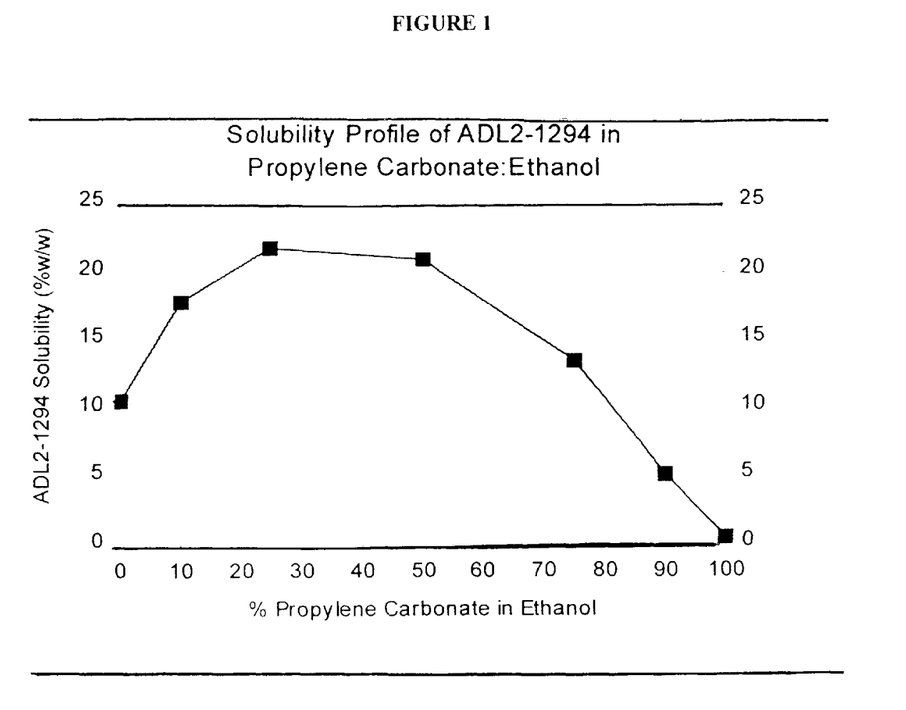
FIG. 1 is a graph showing solubility of loperamide hydrochloride in different ratios of propylene carbonate and ethanol.
Figure 2:
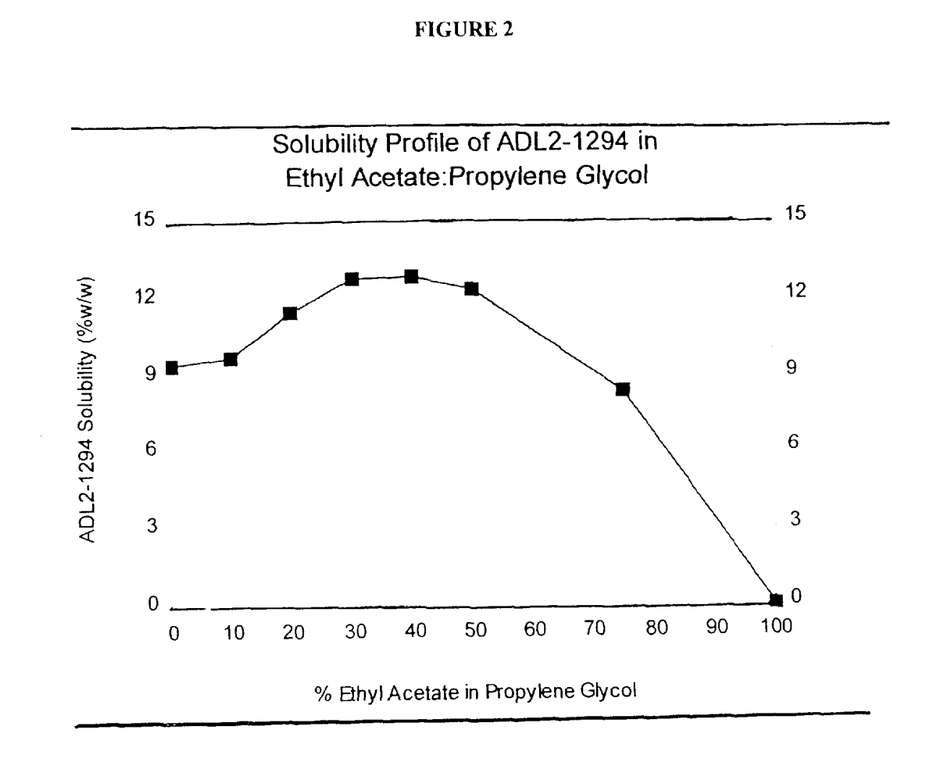
FIG. 2 is a graph showing the solubility of loperamide hydrochloride in ethyl acetate and propylene glycol.

A surprising and unexpected increase in solubility of loperamide hydrochloride was discovered upon blending certain solvent systems. For example, the solubility of loperamide hydrochloride in propylene carbonate was shown to round up to 0.1% (w/w), while solubility of loperamide hydrochloride in ethanol was 10% (w/w). However, a 50% propylene carbonate and 50% ethanol solvent blend dissolved 30% (w/w) loperamide hydrochloride (FIG. 1). The solubility of loperamide hydrochloride in propylene glycol was 8% (w/w) while solubility of loperamide hydrochloride in ethyl acetate rounded up to 0.05% (w/w), but a 60/40 propylene glycol/ethyl acetate solvent blend dissolved 18% (w/w) loperamide hydrochloride (FIG. 2).

Figure 3:
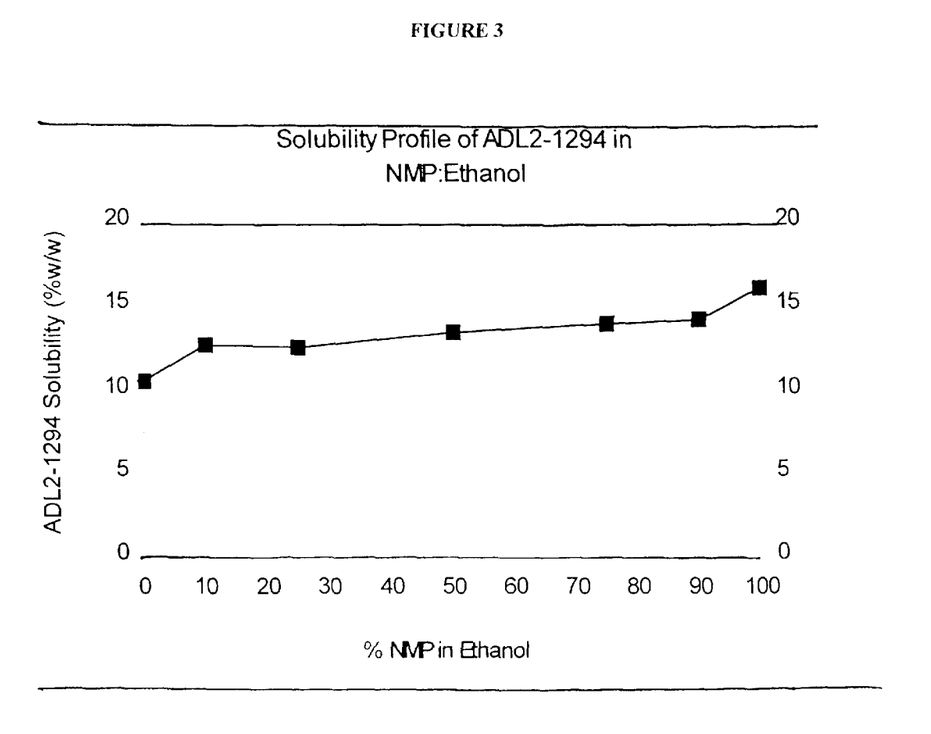
FIG. 3 is a graph showing the solubility of loperamide hydrochloride in ratios of N-methyl-2-pyrrolidone (NMP) and ethanol.
Figure 4:
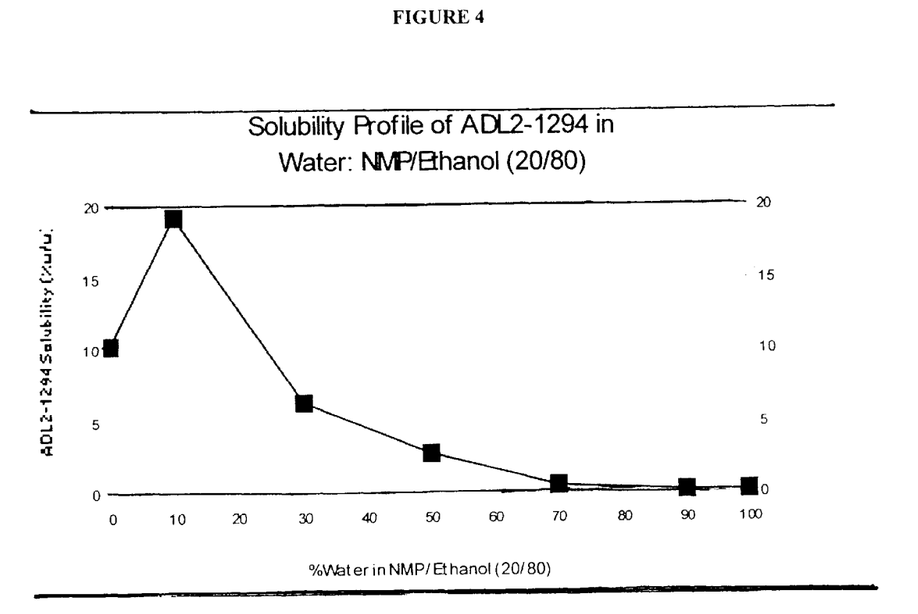
FIG. 4 is a graph showing the solubility of loperamide hydrochloride in ratios of water and the 20:80 solvent blend of N-methyl-2-pyrrolidone (NMP) and ethanol.

This same surprising and unexpected increase in loperamide hydrochloride solubility was also found for ternary blends of solvents. As seen in FIG. 3, the blend of N-methyl-2-pyrrolidone and ethanol did not result in any unexpected increase in loperamide hydrochloride solubility. While some non-ideal solvent behavior is observed at blend ratios near each of the pure solvents, this behavior is not sufficiently great to be surprising. Upon addition of water to a 20:80 N-methyl-2-pyrrolidone:ethanol blend a surprising and unexpected loperamide hydrochloride solubility increase does occur with a 10% (v/v) water, 18% (v/v) N-methyl-2-pyrrolidone and 72% (v/v) ethanol ternary solvent blend dissolving 19% (w/w) loperamide hydrochloride (FIG. 4). Other mixtures and loperamide hydrochloride solubilities are shown in results discussed below.

Figure 5:
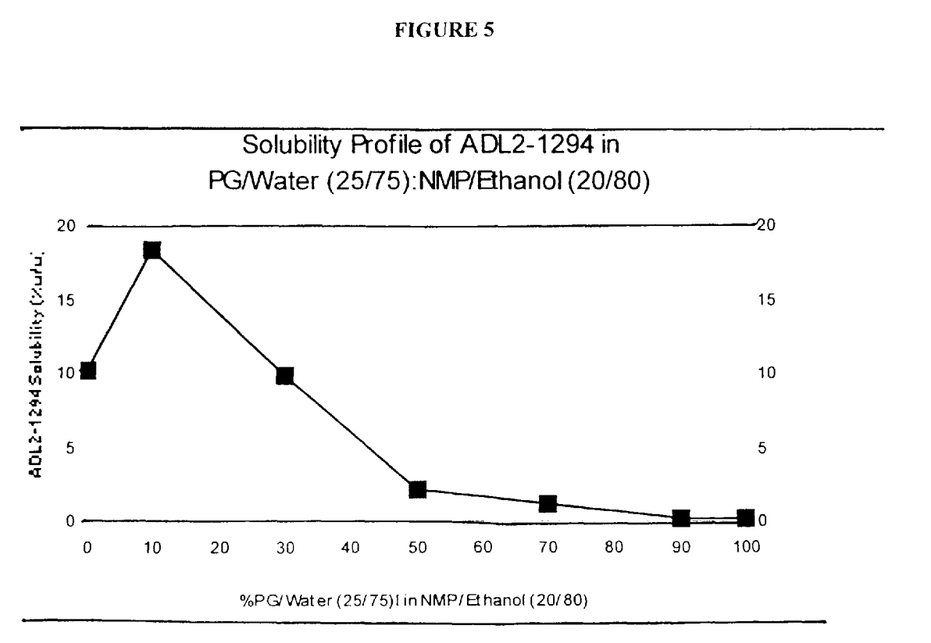
FIG. 5 is a graph showing the solubility of loperamide hydrochloride in ratios of the 25:75 solvent blend of propylene glycol (PG) and water when mixed with the 20:80 solvent blend of N-methyl-2-pyrrolidone (NMP) and ethanol.

As an example of using a four solvent system the 25:75 blend of propylene glycol:water was mixed in different ratios with the 20:80 blend of N-methyl-2-pyrrolidone and ethanol. These four component solvent blends were then saturated with loperamide hydrochloride. As seen in FIG. 5 up to 40% of the 25:75 PG:water blend could be added to the 20:80 NMP:ethanol mix with greater than 5% (w/w) loperamide hydrochloride solubility being maintained, i.e. up to 30% water in the four component solvent blend.

The increased loperamide hydrochloride solubility upon addition of a high water content solvent blend is a surprising and unexpected result (FIG. 5). Other mixtures and loperamide hydrochloride solubilities are shown in results discussed below.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1
Testing Methodology

The solubility studies of loperamide hydrochloride were initiated using the formulation systems shown in Table I through multiple titrations confirmned by HPLC analysis of saturated solutions. For systems having at least 5% loperamide hydrochloride solubility, the transport of loperamide hydrochloride across the skin was characterized by 500 μL and 20 μL dosing of excised human cadaver skin using a Franz in vitro skin diffusion cell.

Example 2
Solubility

Solvent systems were mixed according to weight. For combinations of solvents that were single phase, loperamide hydrochloride was added in 0.1% increments until the system clouded. This was taken as the approximate saturation value for loperamide hydrochloride in that system. The system was then allowed to remain undisturbed for at least 24 hours. Often large crystals of loperamide hydrochloride would form upon standing. This solution was then filtered, appropriately diluted and assayed according to the HPLC method described below.

Example 3
In Vitro Skin Permeation

A standard Franz type vertical diffusion cell (see T. Franz, Percutaneous Absorption. "On the Relevance of In Vitro Data" in *J Invest. Dermatol.*, 64: 190–195, 1975) having a 15 mm orifice, 7.0 mL volume, and equipped with a Hansen Helix stirrer was loaded with excised human skin using 10% N-methyl-2-pyrrolidone in water as the receptor phase. Dermatomed human skin was obtained from the LifeCell Corporation, The Woodlands, Tex. The depth of the dermatome was set so that the skin was removed at the dermal/epidermal junction, i.e., midway through the dermal papillae. Thus, drug partitioning into the receptor solution represents drug that reaches the dermal/epidermal junction. Each 5×15 cm section was placed in a sterile WHIRL-PAK bag (WHIRL-PAK is a registered trademark of Nasco, Ft. Atkinson, Wis.) and stored on wet ice until being placed in the freezer. A single 5×15 cm section of skin was removed from the freezer on the day of an in vitro skin permeation study. Skin was not used if stored frozen for more than six months. After thawing, the skin was rinsed, patted dry with a tissue and loaded on the Franz diffusion cell. Receptor solutions were assayed by reversed phase HPLC using UV detection at 220 nm.

The 64% (v/v) methanol, 36% (v/v) 50 mM potassium phosphate pH 3.0 buffer isocratic mobile phase was pumped at a flow rate of 1.5 mL/min. The column used was a ZORBAX Eclipse XDB-C18 7.5 cm×4.6 mm column having a 3.5 micron packing (ZORBAX is a registered trademark of E. I. du Pont de Nemours and Company, Wilmington, Del.). A guard column was used with the injection volume being 20 μL and a run time of five minutes.

Example 4
Dosing Solutions

For infinite dose experiments 500 μL of the mixed solvent system was applied to the surface of the skin, and the cell was capped. For finite dose experiments, 20 μL of mixed solvent was applied at study initiation, after 16 hours, and after 24 hours. For finite dose experiments the cells remained open to ambient conditions for the duration of the experiment.

Example 5
Receptor Solution

The receptor solution was 10% (v/v) N-methyl-2-pyrrolidone in water. Quantification of the spiked receptor solutions indicate that the solubility of loperamide hydrochloride was greater than 380 ppm. These results indicate that the receptor solution provides sink conditions for loperamide hydrochloride.

Example 6
Loperamide Hydrochloride Solubility in Non-aqueous Solvents and Solvent Mixtures In order to determine which of the formulations had the greatest likelihood of dissolving at least 1% (w/w) loperamide hydrochloride and preferably at least 5% (w/w) loperamide hydrochloride, the solubility of loperamide hydrochloride in the solvents prior to the addition of water was determined. Results are shown in Table 1. Except for N-methyl-2-pyrrolidone, ethanol, and propylene glycol, the solubility of loperamide hydrochloride in the solvents was about 0.5% (w/w) and below. These values are similar to the solubility of loperamide hydrochloride in water which under ambient conditions is about 0.1% (w/w).

TABLE 1

Solubility of loperamide hydrochloride in non-aqueous single component solvents.

| Solvent | Loperamide hydrochloride Solubility (w/w) |
| --- | --- |
| N-methyl-2-pyrrolidone | 16% |
| Ethanol | 10% |
| Propylene Glycol | 9% |
| Propylene Carbonate | 0.5% |
| Water | 0.1% |
| Ethyl Acetate | 0.02% |
| Isopropyl Myristate | 0.001% |

Example 7
Loperamide Hydrochloride Solubility in Aqueous Solvent Mixtures

As seen in FIGS. 1 and 2 the combination of solvents resulted in dramatic increases in loperamide hydrochloride solubility. For the combination of propylene carbonate and ethanol the solubility of loperamide hydrochloride exceeded 20% (w/w). This is especially dramatic since the propylene carbonate as a pure solvent cannot dissolve over 0.5% (w/w) loperamide hydrochloride. A significant increase was also seen for blends of ethyl acetate and propylene glycol (FIG. 2). These results can be contrasted to binary mixtures of N-methyl-2-pyrrolidone and ethanol that have nearly linear changes in loperamide hydrochloride solubility as the amount of one solvent is added to the other.

For blends of three and four solvents dramatic increases in loperamide hydrochloride can also be seen (FIGS. 4 and 5). As water is added to a 20/80 blend of N-methyl-2-pyrrolidone and ethanol a spike in loperamide hydrochloride solubility occurs at about 10% (v/v) water. Again almost a doubling in loperamide hydrochloride solubility can be achieved by appropriately blending three pharmaceutically acceptable solvents (FIG. 4). Loperamide hydrochloride solubility is also significantly increased in four solvent blends as seen in FIG. 5. Addition of propylene glycol allows for loperamide hydrochloride solubility to be maintained above 5% (w/w) at water concentrations up to 30% (w/w). This high level of loperamide hydrochloride solubility is maintained despite N-methyl-2-pyrrolidone (16% (w/w) loperamide hydrochloride solubility) being replaced by propylene glycol (9% (w/w) loperamide hydrochloride solubility).

Example 8

Selection of Solvent Mixtures for in vitro Skin Transport Studies

The solvent mixtures that have the greatest loperamide hydrochloride solubility were further evaluated using the in vitro skin permeation techniques described above. Since oleic acid and oleyl alcohol are skin penetration enhancers for loperamide hydrochloride, the solubility of these two substances in the mixed solvent systems is important. It was generally found that solvent systems containing 30% (w/w) or greater amounts of ethanol could dissolve 1% (w/w) or greater of oleic acid or oleyl alcohol.

Example 9

In vitro Skin Permeation of Loperamide Hydrochloride from Solvent Mixtures without Enhancers In vitro permeation studies must be carefully controlled due to skin from different donors, or skin from the same donor but from different anatomical sites, providing significantly different skin permeation values. Thus, a cream formulation of 5% (w/w) loperamide hydrochloride known as ADL-2-1294-B was used as the control for all infinite dose skin permeation studies. Because the ADL-2-1294-B cream did not provide sufficient transport of loperamide hydrochloride when applied as a finite dose, i.e. 20 microliters, a different control was used for finite dose experiments. The 70:30 propylene glycol:ethyl acetate solution which provided approximately 100-fold greater transport than the ADL-2-1294-B cream was used as the control for all finite dose experiments. Enhancement factor is the percentage of applied dose permeated after 24 hours for the system divided by the percentage of applied dose permeated after 24 hours for the control. An enhancement factor of 1.0 means the system tested had skin permeation equal to the control. Values greater than one indicates an increase in loperamide hydrochloride permeation from the system compared to the control.

As seen in Table 2 the mixed solvent systems tested provided greater skin permeation than the ADL-2-1294-B cream. While many of the systems that had 50-fold loperamide hydrochloride permeation increases contained ethanol, the 90:10 ethanol:water blend only provided modest enhancement (3–13 fold). This indicates that ethanol alone is capable of only modest enhancement, but that it is the combination of ethanol with other pharmaceutically acceptable solvents that provides dramatic enhancement of loperamide hydrochloride skin permeability.

TABLE 2

Figure 6:
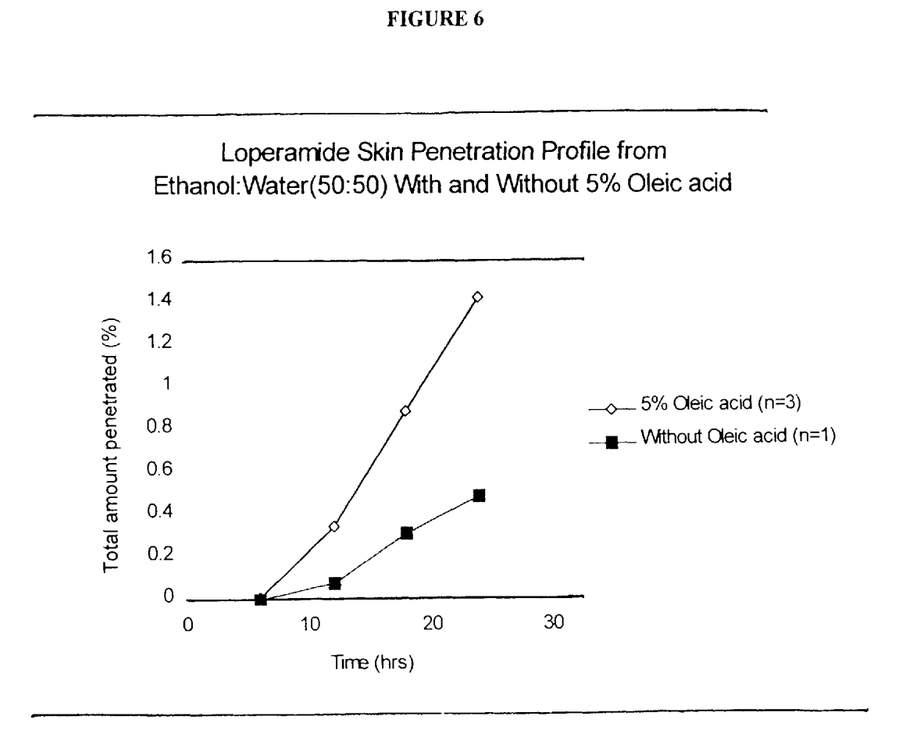
FIG. 6 is a graph showing the skin penetration profile of loperamide hydrochloride from ethanol:water (50:50) with and without 5% oleic acid.
Figure 7:
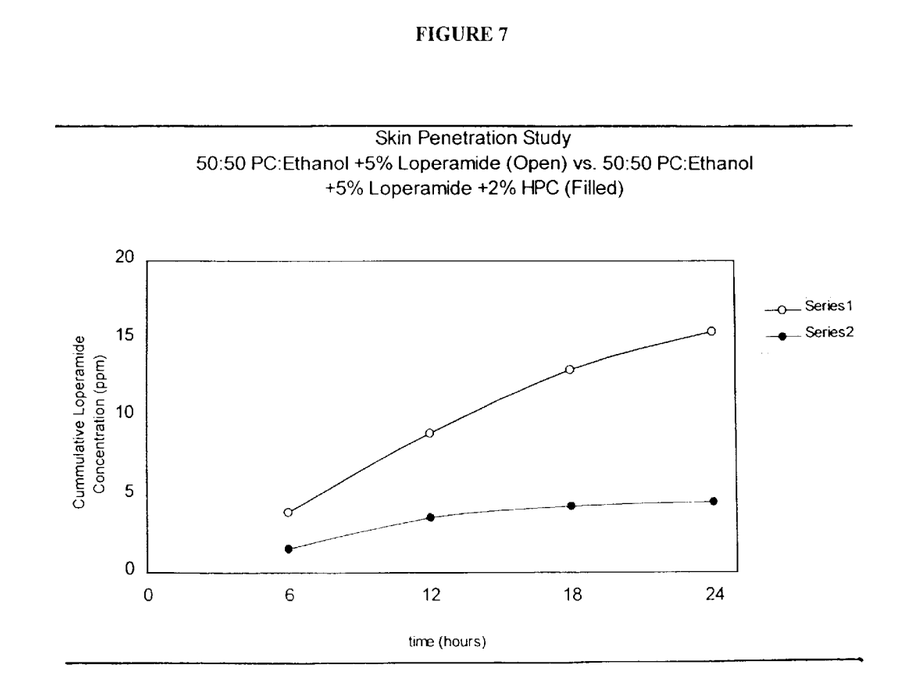
FIG. 7 is a graph showing that addition of the gelling agent hydroxypropyl cellulose reduces skin permeation of loperamide hydrochloride by only about fifty percent for the propylene carbonate:ethanol (50:50) solvent system.
Figure 8:
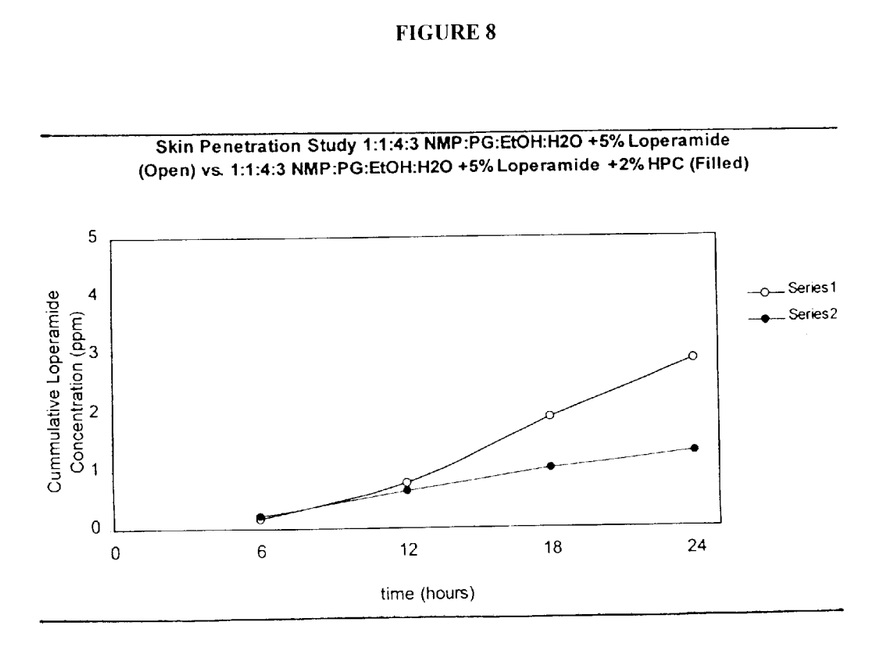
FIG. 8 is a graph showing that addition of the gelling agent hydroxypropyl cellulose reduces skin permeation by only about fifty percent for the 1:1:4:3 N-methyl-2-pyrrolidone:propylene glycol:ethanol:water solvent system.

In vitro skin permeation results for solvent systems with 5% (w/w) added loperamide hydrochlonde

| Solvent system | | Dose | Replicants | Enhancement factor |
|---|---|---|---|---|
| 70:30 PG:EtAc | ADL-2-1294B cream, 5% ADL | Infinite | 4 | 119.2 |
| 60:40 EtOH:IPM | ADL-2-1294B cream, 5% ADL | Infinite | 4 | 86.6 |
| 90:10 EtOH:$H_2O$ | ADL-2-1294B cream, 5% ADL | Infinite | 3 | 2.9 |
| 90:10 EtOH: NMP | ADL-2-1294B cream, 5% ADL | Infinite | 4 | 76.2 |
| 4:1:3 EtOH: NMP:$H_2O$ | ADL-2-1294B cream, 5% ADL | Infinite | 4 | 134.1 |
| 90:10 PC:EtOH | ADL-2-1294B cream, 5% ADL | Infinite | 4 | 3.9 |
| 50:50 PC:EtOH | ADL-2-1294B cream, 5% ADL | Infinite | 3 | 84.6 |
| 90:10 EtOH:$H_2O$ | ADL-2-1294B cream, 5% ADL | Infinite | 3 | 13.8 |
| 90:10 EtOH: $H_2O$ + 5% Oleyl Alcohol | ADL-2-1294B cream, 5% ADL | Infinite | 4 | 146 |
| 1:1:4:3 NMP: PG:EtOH:$H_2O$ | ADL-2-1294B cream, 5% ADL | Infinite | 4 | 214.6 |
| 1:1:4:5 NMP: EtAc:EtOH:$H_2O$ | ADL-2-1294B cream, 5% ADL | Infinite | 3 | 42.7 |
| 50:50 NMP: EtOH | 70:30 PG:EtAc + 5% ADL | Finite | 3 | 7.199 |
| 1:1:1 PG:EtOH: EtAc | 70:30 PG:EtAc + 5% ADL | Finite | 2 | 1.780 |
| 50:50 PC:EtOH | 70:30 PG:EtAc + 5% ADL | Finite | 4 | 0.754 |
| 1:1:4:3 NMP: PG:EtOH:$H_2O$ | 70:30 PG:EtAc + 5% ADL | Finite | 2 | 2.319 |
| 1:1:4:5 NMP: EtAc: EtOH:$H_2O$ | 70:30 PG:EtAc + 5% ADL | Finite | 2 | 1.762 |

Aqueous and nonaqueous solvent systems containing ethanol that gave the highest solubility and delivery of loperamide hydrochloride across intact skin included additional solvents such as N-methyl-2-pyrrolidone, propylene glycol, and propylene carbonate. Specifically, four mixed solvent systems illustrated excellent transport of loperamide hydrochloride across the skin. The first solvent system contained approximately 50% (v/v) propylene carbonate, and 50% (v/v) ethanol. The system could dissolve up to 21% (w/w) loperamide hydrochloride. The second mixed solvent system contained 1:1:1 propylene glycol:ethanol:ethyl acetate. This system could dissolve greater than 5% (w/w) loperamide hydrochloride and in a finite dose experiment provided about twice the skin permeation of the control. A third mixed solvent system, provided a good vehicle for loperamide hydrochloride to penetrate the skin providing twice the permeation of the control. This system was 1:1:4:3 N-methyl-2-pyrrolidone:propylene glycol:alcohol:water mixture and could dissolve greater than 6% (w/w) loperamide hydrochloride. The fourth system was 1:1:4:5 N-methyl-2-pyrrolidone:ethyl acetate:ethanol:water which dissolved greater than 5% (w/w) loperamide hydrochloride and in a finite dose experiment provided about twice the skin permeation of the control.

Example 10

In vitro Skin Permeation of Loperamide Hydrochloride from Solvent Mixtures with Enhancers Oleic acid and oleyl alcohol were added to ethanol:water mixtures. His seen in FIGS. 6 and 7 the addition of 5% of oleic acid or 5% oleyl alcohol to the ethanol:water system significantly increased loperamide hydrochloride permeation. As shown in Table 2, the addition of 5% oleyl alcohol to the 90:10 (v/v) ethanol:water solvent system provides about a 100-fold increase in permeation of loperamide hydrochloride across the skin over 24 hours when an infinite dose (500 IL) of the solvent system is applied. When oleic acid is used (FIG. 6) in a 50:50 (v/v) ethanol:water solvent system and applied as a finite dose, a three-fold increase in skin permeation of loperamide hydrochloride occurs over 24 hours.

Ultimately, topical formulations require additional excipients in addition to the solvent system and actives. These additional components include preservatives and gelling agents. While preservatives rarely alter the skin permeation of actives, the use of gelling agents, especially for solvent systems that are not predominately water, requires evaluation of loperamide hydrochloride permeability with and without gelling agents being present in the formulation. The 50:50 propylene carbonate:ethanol system readily gelled by use of hydroxypropyl cellulose. The use of 2% (w/w) of this gelling agent resulted in about a 50% reduction in loperamide hydrochloride skin permeation (FIG. 7). Likewise, the 2% (w/w) hydroxypropyl cellulose gel of the 1:1:4:3 N-methyl-2-pyrrolidone:proylene glycol:ethanol:water solvent system resulted in about a 50% reduction in loperamide hydrochloride skin permeation compared with the non-gelled solvent system (FIG. 8). This reduction in loperamide hydrochloride skin permeation is consistent with differences for fluid versus viscous topical formulations (see D. W. Osborne and A. J. I. Ward, "Lyotropic Liquid Crystals as Topical Drug Delivery Vehicles" in *Int'l J of Pharm Advances,* 1: 38–45, 1995). Thus, the gelling of these solvent systems as required for aesthetically acceptable topicals does not unreasonably decrease the skin permeability of loperamide hydrochloride.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A composition comprising loperamide hydrochloride dissolved in a mixture of propylene carbonate and ethanol, wherein the concentration of dissolved loperamide hydrochloride is at least about 1% (w/w) of the composition.

2. The composition of claim 1, wherein the loperamide hydrochloride has an in vitro rate of penetration through the stratum corneum of at least about 0.3 μg per $cm^2$ per hour.

3. The composition of claim 1, further comprising a hydrotropic agent selected from the group consisting of isopropyl alcohol, propylene glycol, and sodium xylene sulfonate.

4. The composition of claim 1, further comprising an opioid analgesic selected from the group consisting of morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, and butorphanol.

5. The composition of claim 1, further comprising moisturizers, humectants, oils, emulsifiers, thickeners, thinners, surface active agents, fragrances, preservatives, antioxidants, vitamins, or minerals.

6. The composition of claim 1, further comprising a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

7. The composition of claim 6, wherein the penetration enhancer is oleic acid or oleyl alcohol.

8. A composition comprising loperamide hydrochloride dissolved in a mixture of propylene glycol and ethyl acetate, wherein the concentration of dissolved loperamide hydrochloride is at least about 1% (w/w) of the composition.

9. The composition of claim 8, wherein the loperamide hydrochloride has an in vitro rate of penetration through the stratum corneum of at least about 0.3 μg per $cm^2$ per hour.

10. The composition of claim 8, further comprising a hydrotropic agent selected from the group consisting of isopropyl alcohol, propylene glycol and sodium xylene sulfonate.

11. The composition of claim 8, further comprising an opioid analgesic selected from the group consisting of morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, and butorphanol.

12. The composition of claim 8, further comprising moisturizers, humectants, oils, emulsifiers, thickeners, thinners, surface active agents, fragrances, preservatives, antioxidants, vitamins, or minerals.

13. The composition of claim 8, further comprising a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

14. The composition of claim 13, wherein the penetration enhancer is oleic acid or oleyl alcohol.

15. A composition comprising loperamide hydrochloride dissolved in a mixture of N-methyl-2-pyrrolidone and ethanol, wherein the concentration of dissolved loperamide hydrochloride is at least about 1% (w/w) of the composition.

16. The composition of claim 15, wherein the loperamide hydrochloride has an in vitro rate of penetration through the stratum corneum of at least about 0.3 g per $cm^2$ per hour.

17. The composition of claim 15, further comprising a hydrotropic agent selected from the group consisting of isopropyl alcohol, propylene glycol and sodium xylene sulfonate.

18. The composition of claim 15, further comprising an opioid analgesic selected from the group consisting of morphine, heroin, hydromorphine, oxymorphine, levorphanol, methadonc, meperidine, fentanyl, codeine, hydrocodone, drocode, oxycodone, propoxyphene, buprenorphine, pentazocine, nalbuphine, and butorphanol.

19. The composition of claim 15, further comprising moisturizers, humectants, oils, emulsifiers, thickeners, thinners, surface active agents, fragrances, preservatives, antioxidants, vitamins, or minerals.

20. The composition of claim 15, further comprising water.

21. The composition of claim 15, further comprising water and propylene glycol.

22. The composition of claim 15, further comprising a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

23. The composition of claim 22, wherein the penetration enhancer is oleic acid or oleyl alcohol.

24. A method of inducing analgesia or antihyperalgesia in humans, comprising topically applying a composition to the skin in a dosage effective to cause analgesia or antihyperalgesia, wherein:

the composition comprises loperamide hydrochloride dissolved in a mixture of propylene carbonate and ethanol;

the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour.

25. The method of claim 24, wherein the composition further comprises a hydrotropic agent selected from the group consisting of isopropyl alcohol, propylene glycol and sodium xylene sulfonate.

26. The method of claim 24, wherein the composition further comprises an opioid analgesic selected from the group consisting of morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, and butorphanol.

27. The method of claim 24, wherein the composition further comprises moisturizers, humectants, oils, emulsifiers, thickeners, thinners, surface active agents, fragrances, preservatives, antioxidants, vitamins, or minerals.

28. The method of claim 24, wherein the composition further comprises a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

29. The method of claim 28, wherein the penetration enhancer is oleic acid or oleyl alcohol.

30. A method of inducing analgesia or antihyperalgesia in humans, comprising topically applying a composition to the skin in a dosage effective to cause analgesia or antihyperalgesia, wherein:

the composition comprises loperamide hydrochloride dissolved in a mixture of propylene glycol and ethyl acetate;

the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour.

31. The method of claim 30, wherein the composition further comprises a hydrotropic agent selected from the group consisting of isopropyl alcohol, propylene glycol and sodium xylene sulfonate.

32. The method of claim 30, wherein the composition further comprises an opioid analgesic selected from the group consisting of morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, and butorphanol.

33. The method of claim 30, wherein the composition further comprises moisturizers, humectants, oils, emulsifiers, thickeners, thinners, surface active agents, fragrances, preservatives, antioxidants, vitamins, or minerals.

34. The method of claim 30, wherein the composition further comprises a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

35. The method of claim 34, wherein the penetration enhancer is oleic acid or oleyl alcohol.

36. A method of inducing analgesia or antihyperalgesia in humans, comprising topically applying a composition to the skin in a dosage effective to cause analgesia or antihyperalgesia, wherein:

the composition comprises loperamide hydrochloride dissolved in a mixture of N-methyl-2-pyrrolidone and ethanol;

the concentration of dissolved loperamide hydrochloride is at least 1% (w/w) of the composition; and the composition has an in vitro rate of penetration of loperamide hydrochloride through the stratum corneum of at least about 0.3 $\mu$g per cm$^2$ per hour.

37. The method of claim 36, wherein the composition further comprises a hydrotropic agent selected from the group consisting of isopropyl alcohol, propylene glycol and sodium xylene sulfonate.

38. The method of claim 36, wherein the composition further comprises an opioid analgesic selected from the group consisting of morphine, heroin, hydromorphine, oxymorphine, levorphanol, methadone, meperidine, fentanyl, codeine, hydrocodone, drocode, oxycodone, propoxyphene, buprenorphine, pentazocine, nalbuphine, and butorphanol.

39. The method of claim 36, wherein the composition further comprises moisturizers, humectants, oils, emulsifiers, thickeners, thinners, surface active agents, fragrances, preservatives, antioxidants, vitamins, or minerals.

40. The method of claim 36, wherein the composition further comprises water.

41. The method of claim 36, wherein the composition further comprises water and propylene glycol.

42. The method of claim 36, wherein the composition further comprises a penetration enhancer selected from the group consisting of oleic acid, oleyl alcohol, ethoxydiglycol, laurocapram, alkanecarboxylic acids, dimethylsulfoxide, polar lipids, and N-methyl-2-pyrrolidone.

43. The method of claim 42, wherein the penetration enhancer is oleic acid or oleyl alcohol.

* * * * *